(12) United States Patent
Adams et al.

(10) Patent No.: US 10,321,942 B2
(45) Date of Patent: Jun. 18, 2019

(54) COMPRESSION SCREW SYSTEMS FOR COMPRESSING BONES OF THE EXTREMITIES

(71) Applicant: Life Spine, Inc., Huntley, IL (US)

(72) Inventors: Heiko B. Adams, Shelbyville, KY (US); Jacob A. Hord, Louisville, KY (US); Kevin D. Brown, Proctorville, OH (US); Chris W. Hubbard, Louisville, KY (US); Paul J. Klutts, Cox's Creek, KY (US); Daniel P. Predick, Chicago, IL (US); Garrett D. Lauf, Elgin, IL (US)

(73) Assignee: LIFE SPINE, INC., Huntley, IL (US)

( * ) Notice: Subject to any disclaimer, the term of this patent is extended or adjusted under 35 U.S.C. 154(b) by 571 days.

(21) Appl. No.: 14/742,633

(22) Filed: Jun. 17, 2015

(65) Prior Publication Data
US 2015/0359573 A1 Dec. 17, 2015

Related U.S. Application Data

(60) Provisional application No. 62/013,218, filed on Jun. 17, 2014.

(51) Int. Cl.
*A61B 17/72* (2006.01)
*A61B 17/80* (2006.01)
*A61B 17/86* (2006.01)

(52) U.S. Cl.
CPC ........ *A61B 17/7291* (2013.01); *A61B 17/809* (2013.01); *A61B 17/8052* (2013.01); *A61B 17/863* (2013.01); *A61B 17/8695* (2013.01); *A61B 17/8635* (2013.01)

(58) Field of Classification Search
CPC combination set(s) only.
See application file for complete search history.

(56) References Cited

U.S. PATENT DOCUMENTS

| | | | |
|---|---|---|---|
| 3,593,709 A | 7/1971 | Halloran |
| 3,716,050 A | 2/1973 | Johnston |
| 4,454,876 A | 6/1984 | Mears |
| 4,565,193 A | 1/1986 | Streli |
| 4,800,874 A | 1/1989 | David et al. |

(Continued)

*Primary Examiner* — Yashita Sharma
(74) *Attorney, Agent, or Firm* — Foley & Lardner LLP

(57) ABSTRACT

Compression screw systems for stabilizing and/or compressing bones of the extremities, characterized by a compression screw component and a hook component. The hook component is received on the compression screw component in any rotational position relative to the compression screw component in order to orient the hook component relative to a bone or bones requiring stabilization and/or compression. The hook component includes an anti-rotation feature, while a configured flange thereof provides a hook that extends about and overhangs a part of the bone. The compression screw component and the hook component may include cooperating structures that allow the hook component to attach to the compression screw component or allow the compression screw component to self-orientate with respect to the hook component upon compressing engagement of the compression screw head with the hook component. The configured flange of the hook component may terminate with a single, double or multiple tined prong.

16 Claims, 22 Drawing Sheets

(56) References Cited

U.S. PATENT DOCUMENTS

| | | | |
|---|---|---|---|
| 5,261,909 A * | 11/1993 | Sutterlin | A61B 17/7038 |
| | | | 606/264 |
| 5,718,705 A | 2/1998 | Sammarco | |
| 5,810,822 A * | 9/1998 | Mortier | A61B 17/8061 |
| | | | 606/101 |
| 6,283,969 B1 | 9/2001 | Grusin et al. | |
| 8,177,819 B2 * | 5/2012 | Huebner | A61B 17/80 |
| | | | 606/281 |
| 8,403,970 B1 | 3/2013 | Bedor | |
| 9,254,154 B2 | 2/2016 | Gonzalez-Hernandez | |
| 9,402,667 B2 | 8/2016 | Gonzalez-Hernandez | |
| 2003/0055429 A1 | 3/2003 | Ip et al. | |
| 2005/0192577 A1 | 9/2005 | Mosca et al. | |
| 2006/0235396 A1 | 10/2006 | Sanders et al. | |
| 2007/0233113 A1 | 10/2007 | Kaelblein et al. | |
| 2008/0300637 A1 | 12/2008 | Austin et al. | |
| 2009/0118769 A1 | 5/2009 | Sixto et al. | |
| 2010/0217327 A1 | 8/2010 | Vancelette et al. | |
| 2010/0217328 A1 | 8/2010 | Terrill et al. | |
| 2010/0256687 A1 | 10/2010 | Neufeld et al. | |
| 2010/0324602 A1 | 12/2010 | Huebner et al. | |
| 2013/0158608 A1 | 6/2013 | Viola et al. | |
| 2013/0172942 A1 | 7/2013 | Lewis et al. | |
| 2014/0172020 A1 | 6/2014 | Gonzalez-Hernandez | |
| 2014/0249586 A1 | 9/2014 | Guy et al. | |
| 2015/0223851 A1 | 8/2015 | Hill et al. | |

* cited by examiner

COMPRESSION SCREW SYSTEMS FOR COMPRESSING BONES OF THE EXTREMITIES

CROSS-REFERENCE TO RELATED APPLICATIONS

This U.S. non-provisional patent application claims the benefit of and/or priority under 35 U.S.C. § 119(e) to U.S. provisional patent application Ser. No. 62/013,218 filed Jun. 17, 2014 titled "Compression Screw System for Stabilizing and Compressing Bones of the Extremities," the entire contents of which is specifically incorporated herein by reference.

BACKGROUND OF THE INVENTION

Field of the Invention

The present invention relates to implants for fixation of human bones, and particularly to implants for fixation of bones of the extremities. More particularly, the present invention relates to compression screws for stabilizing and compressing bones of the extremities.

Background

Compression screws, both headless and headed, are routinely used for fixing or mending bones of the body. Particularly, and without being exhaustive, compression screws of various lengths are used for fixation of intra-articular and extra-articular fractures, avulsions, non-unions, arthrodesis, osteotomies, and reconstruction of the bones. A fundamental feature of compression screws is the amount of compression the screw achieves. Typically, the greater the compression the better the bone or bones will strongly mend.

While compression screws perform their function of compression, they do not of themselves provide compression and stabilization of the bone or bones. Therefore, either several compression screws are used or a plate or other device is used in conjunction with the compression screw(s). However, the greater number of components, the greater chance for problems.

In view of the above, it would be desirable to have a compression screw system for bones of the extremities that overcomes the deficiencies of the prior art. More particularly, it would be desirable to have a compression screw system that provides compression and stability to bones of the extremities.

SUMMARY OF THE INVENTION

The present invention is a compression screw system and method of use for stabilizing and compressing bones of the extremities. The compression screw system is characterized by a compression screw component and a hook component. The hook component is received on the compression screw component in any rotational position relative to the compression screw component in order to orient the hook component relative to a bone or bones requiring compression. The hook component includes a plurality of teeth on its distal side that provide an anti-rotation feature once the hook component is driven into the bone by the compression screw component, and a configured flange providing a hook that extends about and overhangs a part of the bone.

The head of the compression screw component and the hook component may include cooperating structures that allow the hook component to attach to the compression screw component. In one form, the cooperating structure of the head of the compression screw component comprises an undercut groove, while the cooperating structure of the hook component includes a rib that will 'snap' into the undercut groove of the compression screw component head.

The head of the compression screw component may have cooperating structures that allow the compression screw component to self-orientate with respect to the hook component upon compressing engagement of the compression screw head with the hook component.

The configured flange of the hook component may terminate with a single, double or multiple tined prong. The end of the prong(s)/tines may be blunt or pointed.

In all forms, the compression screw component may have a longitudinal bore that extends from the head of the compression screw component through and to its tip.

The present compression screw systems are configured such that they provide compression in the extremities as an intra-medullary and as an extra-medullary device. The compression screw component alone may be used as a compression screw for intra-medullary use, while the compression screw component and the hook component together are utilized for compression and stabilization for extra-medullary use.

The present compression screw systems thus provide the ability to stabilize and compress factures or the like at various positions with positioning of the hook component and insertion of the compression screw component. Various sizes of the hook component can be placed on various sizes of compression screw components depending on the specific anatomy presented.

Further aspects of the present invention will become apparent from consideration of the drawings and the following description of preferred forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate forms of the invention, wherein.

DETAILED DESCRIPTION OF THE INVENTION

Figure 1:
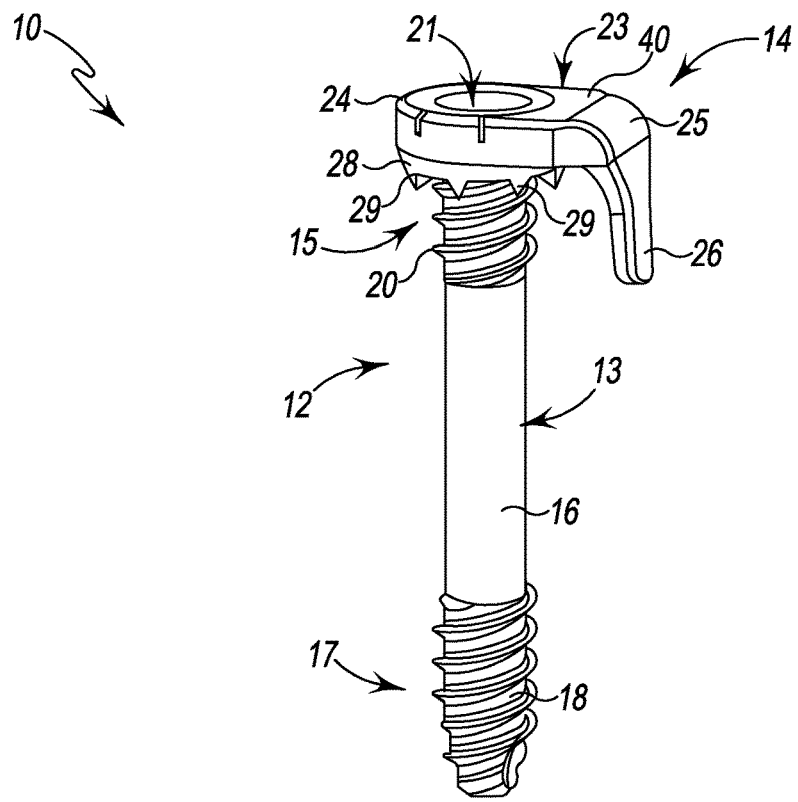
FIG. 1 is an isometric view of a compression screw system for bones of the extremities fashioned in accordance with the principles of the present invention.
Figure 2:
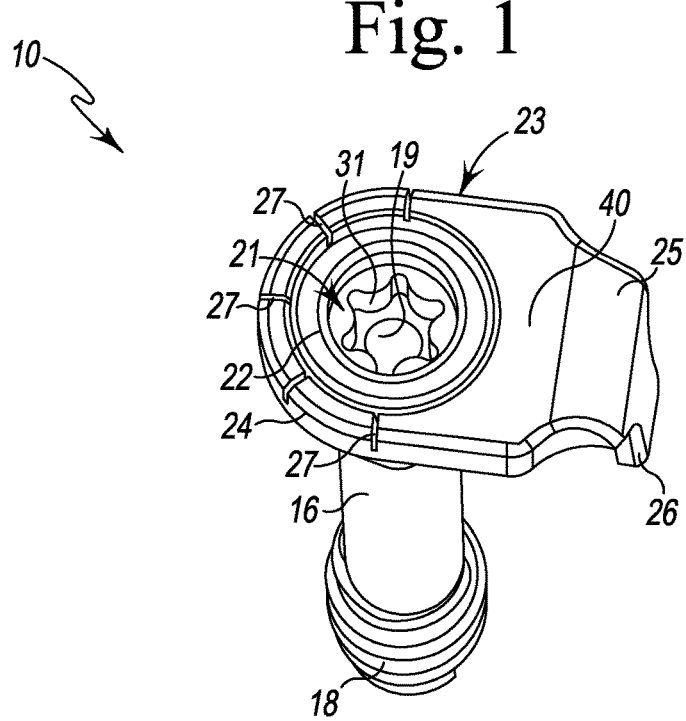
FIG. 2 is a top isometric view of the compression screw system of FIG. 1.
Figure 3:
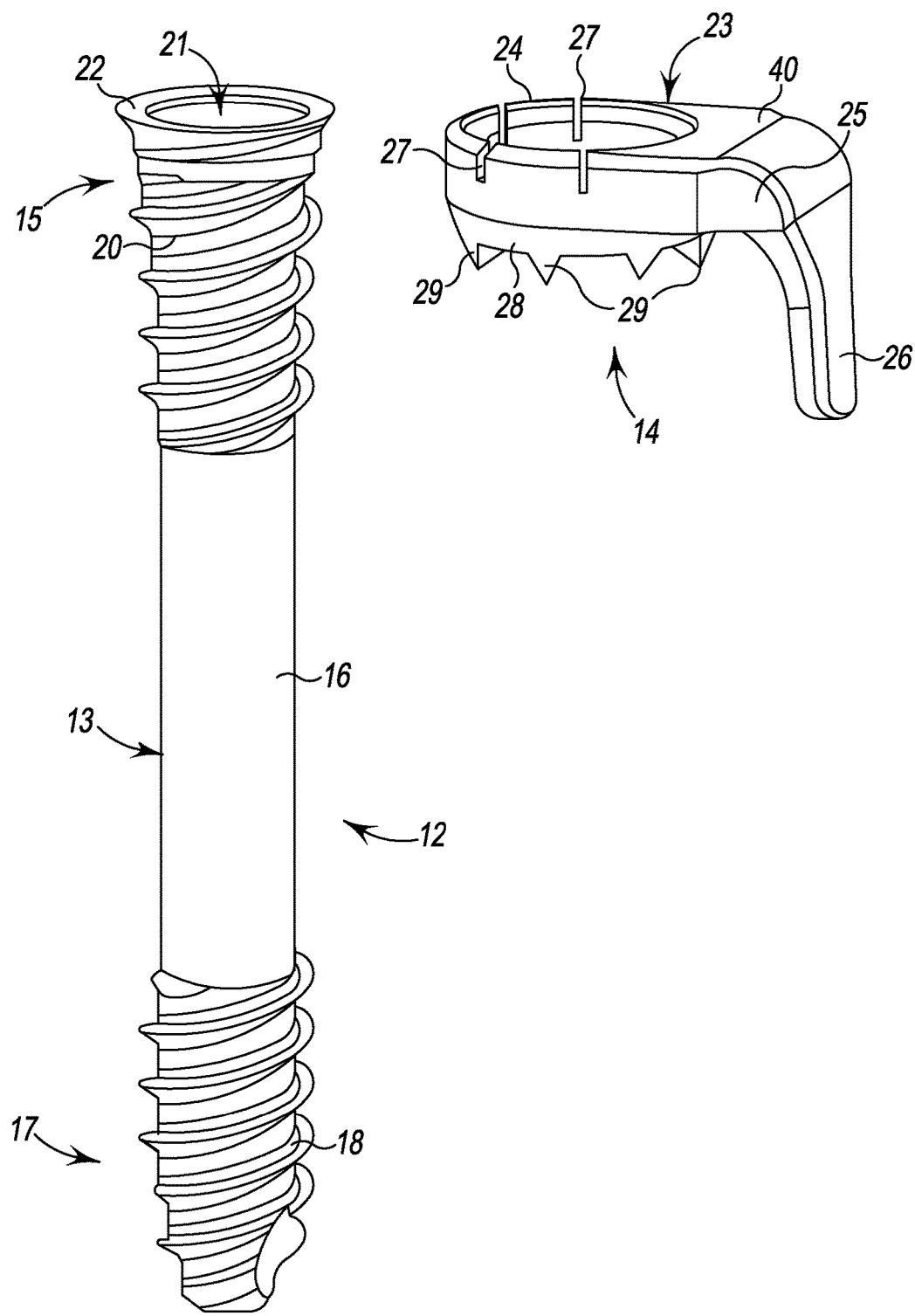
FIG. 3 is an isometric side view of the two components of the compression screw system of FIG. 1.
Figure 4:
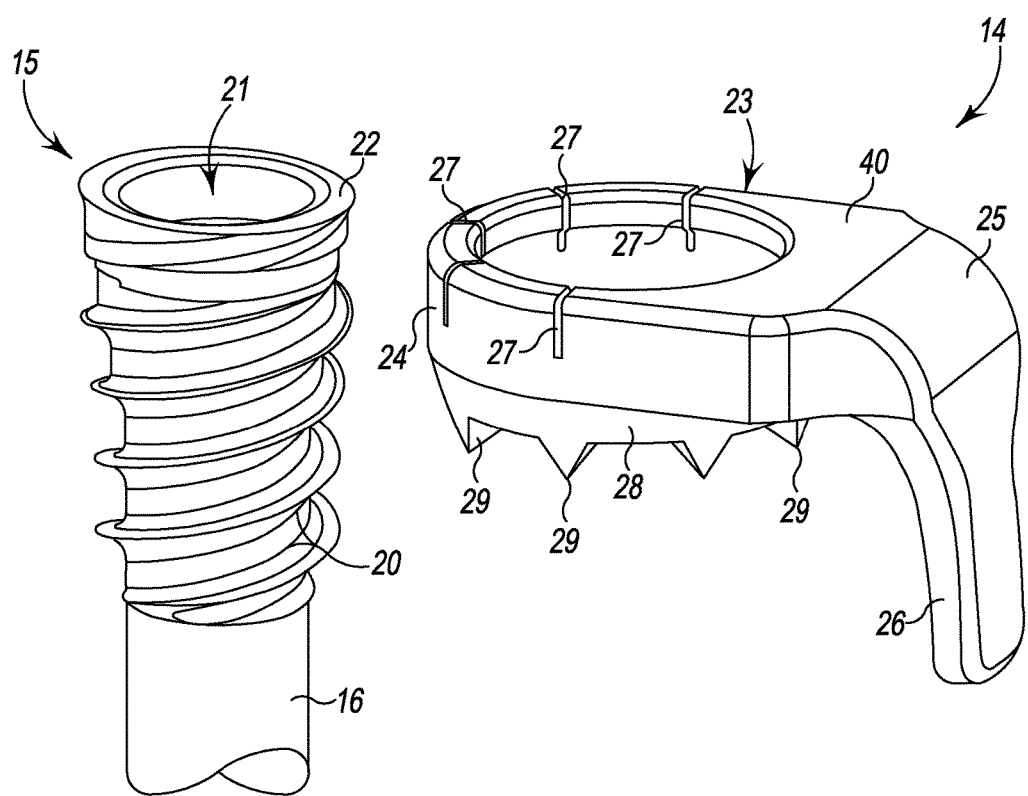
FIG. 4 is an enlarged portion of the two components of the compression screw system as shown in FIG. 3.

Referring to FIGS. 1-7, there is depicted an implant, generally designated 10, for compressing and/or stabilizing a bone or bones of the extremities and, particularly, a compression screw system 10 for stabilizing and/or compressing bone fractures (or the like) of the extremities at various positions. The compression screw system comprises a compression screw component 12 and a hook component 14. The compression screw component 12 and the hook component 14 are fashioned from a known biocompatible implant material.

The compression screw component 12 comprises a bone screw characterized by an elongated body, shaft or shank 13 with a middle portion 16 having a smooth outer surface, a tip 17 having external threads or threading 18, and a head portion 15 having external threads or threading 20. The tip 17 is slightly radially inwardly tapered while the head portion 15 is slightly radially outwardly tapered. The threads or threading 18 of the tip 17 is configured to be preferably self-tapping and of a pitch and radial size that provides good gripping of the bone into which the compression screw component 12 is received. The threads or threading 20 of the head portion 15 is sized of a pitch and radial size that provides good gripping of the bone into which the compression screw component 12 is received.

Figure 6:
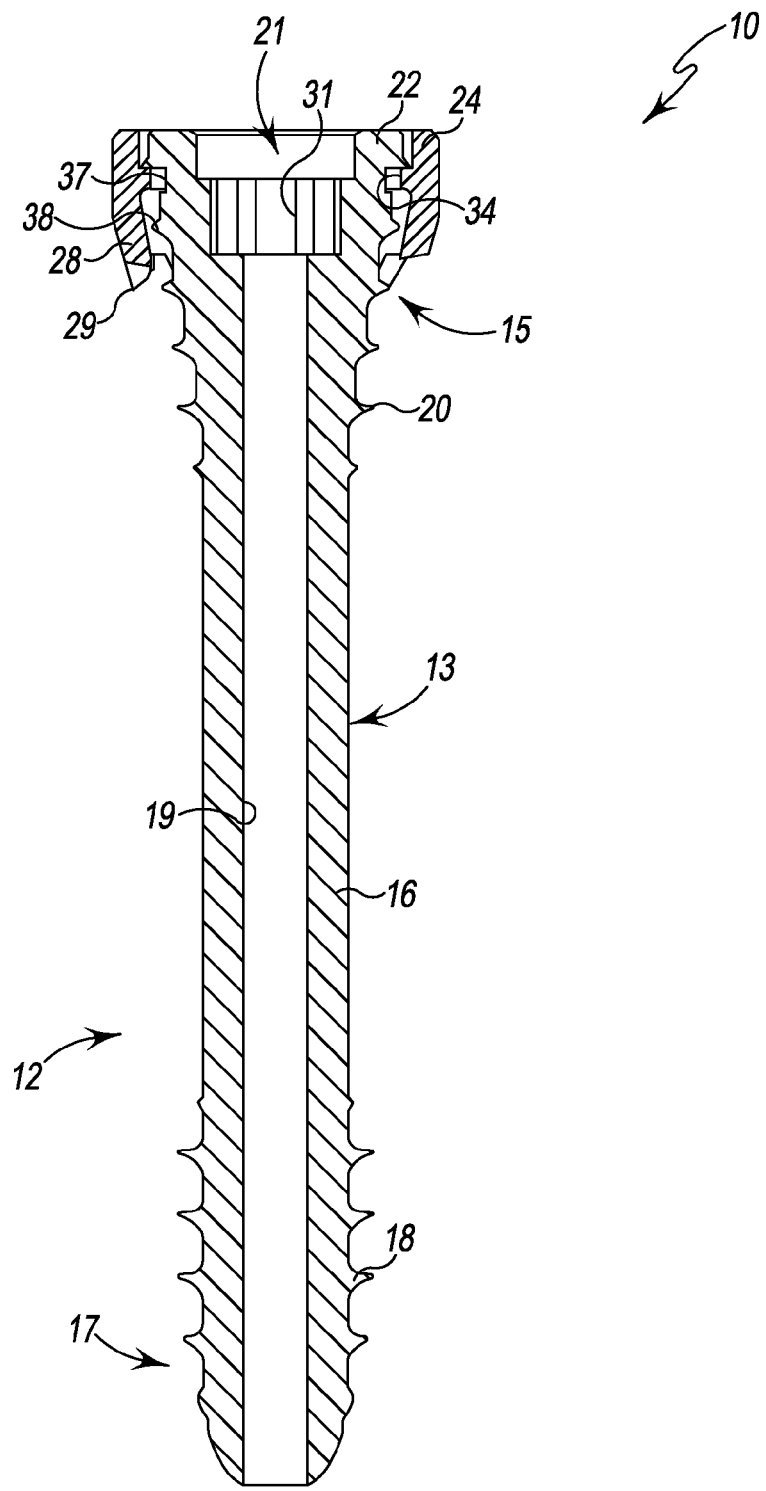
FIG. 6 is an enlarged side sectional view of the compression screw component of the compression screw system of FIG. 1.

A socket 21 is provided in the head portion 15 of the compression screw component 12. The socket 21 has an inner portion 31 that that is configured to receive a working end of a compression screw driver or tool (not shown) such as is known in the art. As best seen in FIG. 6, the compression screw component 12 is hollow, having a longitudinal bore 19 that extends from the socket 21 of the head portion 15 to the tip 17. Moreover, the head portion 15 has a rim 22 that extends about the socket 21, the rim 22 being slightly radially outwardly flared on its periphery.

Figure 7:
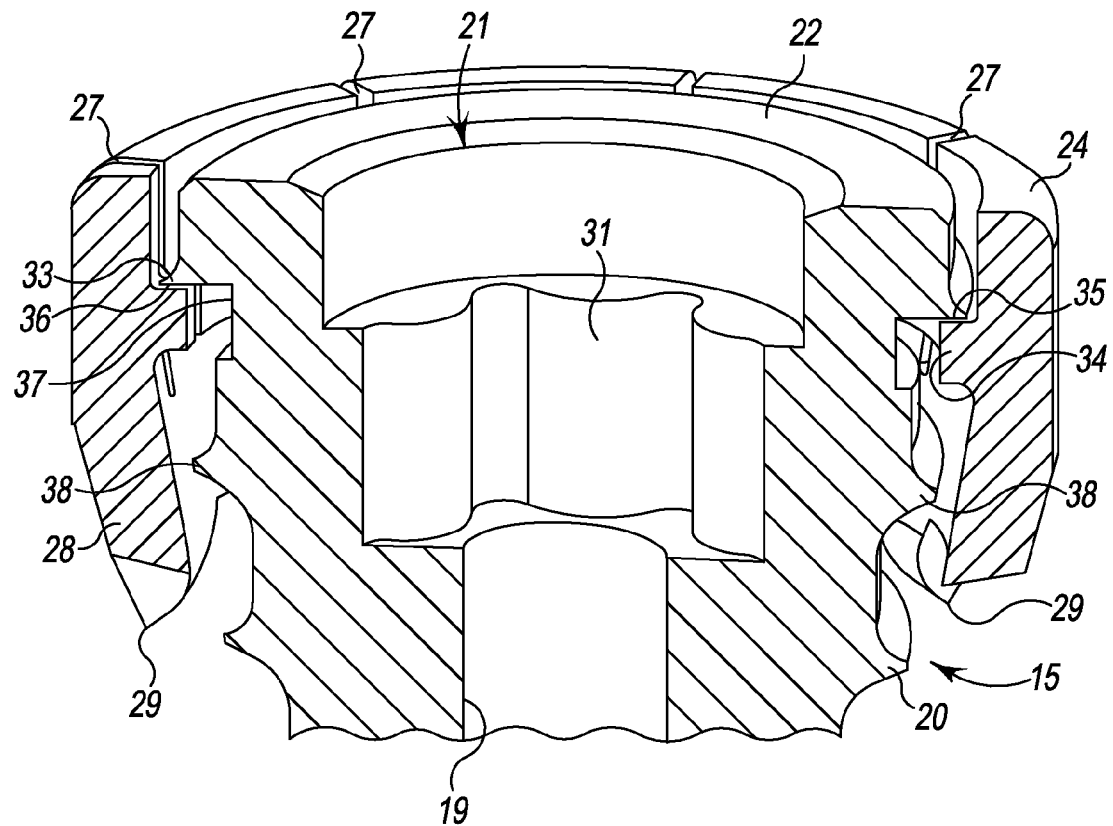
FIG. 7 is an enlarged portion of a sectional view of the head of the hook component of the compression screw system of FIG. 1.
Figure 8:
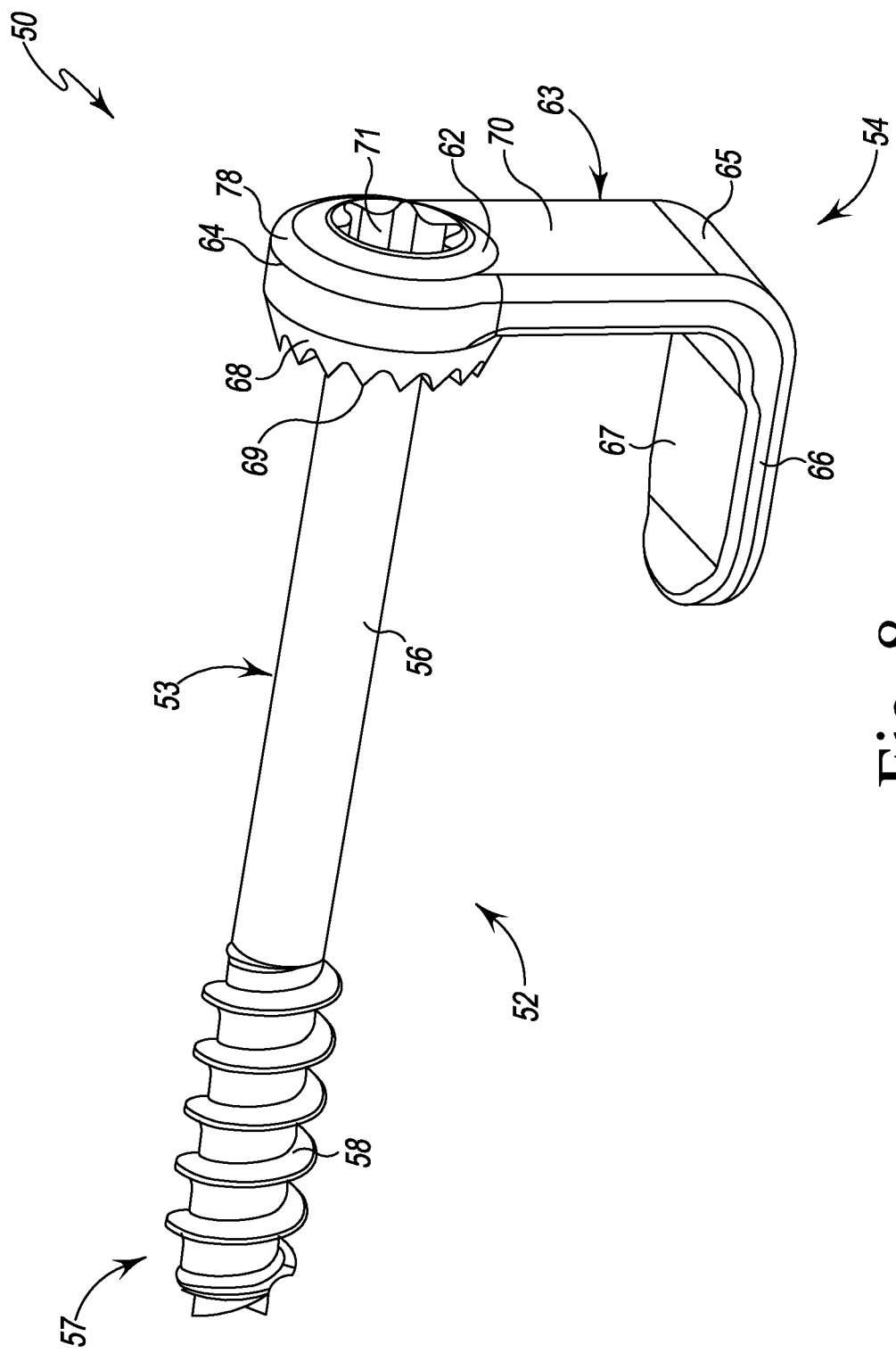
FIG. 8 is an isometric view of a compression screw system for bones of the extremities fashioned in accordance with the principles of the present invention.
Figure 9:
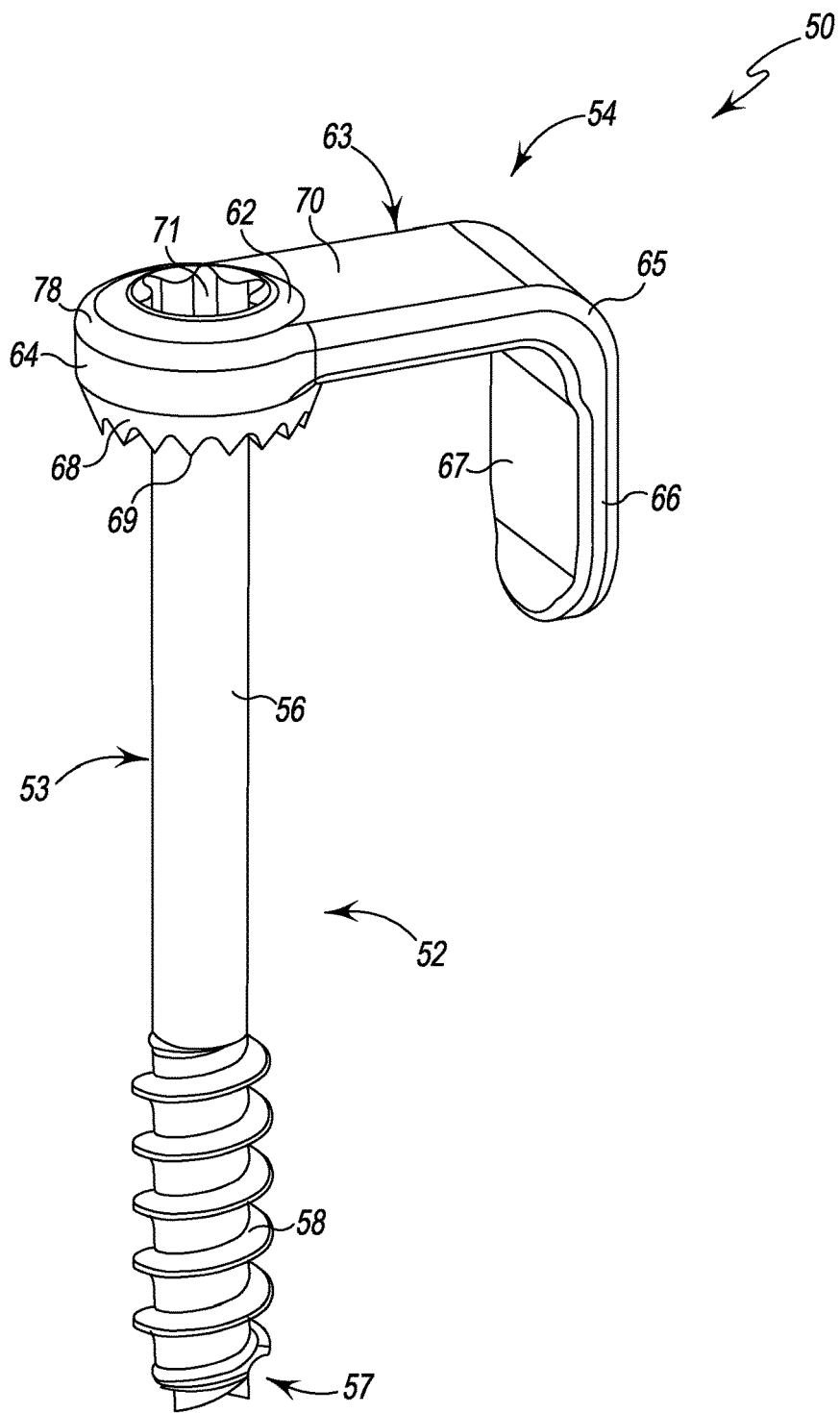
FIG. 9 is another isometric view of the compression screw system of FIG. 8.

As best seen in FIGS. 6 and 7, the head portion 15 (or proximate to the head portion 15) of the compression screw component 12, includes structure which cooperates with structure of the hook component 14 (described in greater detail below) whereby the hook component 14 is captured by the compression screw component 12 when the hook component 14 is loaded onto the compression screw component 12 from the bottom of the compression screw component 12 (see FIG. 5) or vice versa. The cooperating structure of the head portion 15 includes a groove, under cut, or the like 37 that extends radially about the head portion 15. The groove 37 is positioned above the last threading 38 of the head portion 15 and below a radially outwardly flared bottom 33 of the rim 22. The flared bottom 33 projects radially over the groove 37 to define an upper seating ledge 36, both of which may be included as part of the cooperating structure of the head portion 15. The flared bottom 33 and the upper seating ledge 36 provide a stop against further axial travel of the hook component 14 relative to the compression screw component 12 and/or vice versa, and to allow the compression screw component 12 to push against or provide compression to the hook component 14. In this manner, driving the compression screw component 12 into the extremity bones also secures the hook component 14 at and to the desired portion of an extremity bone.

Figure 5:
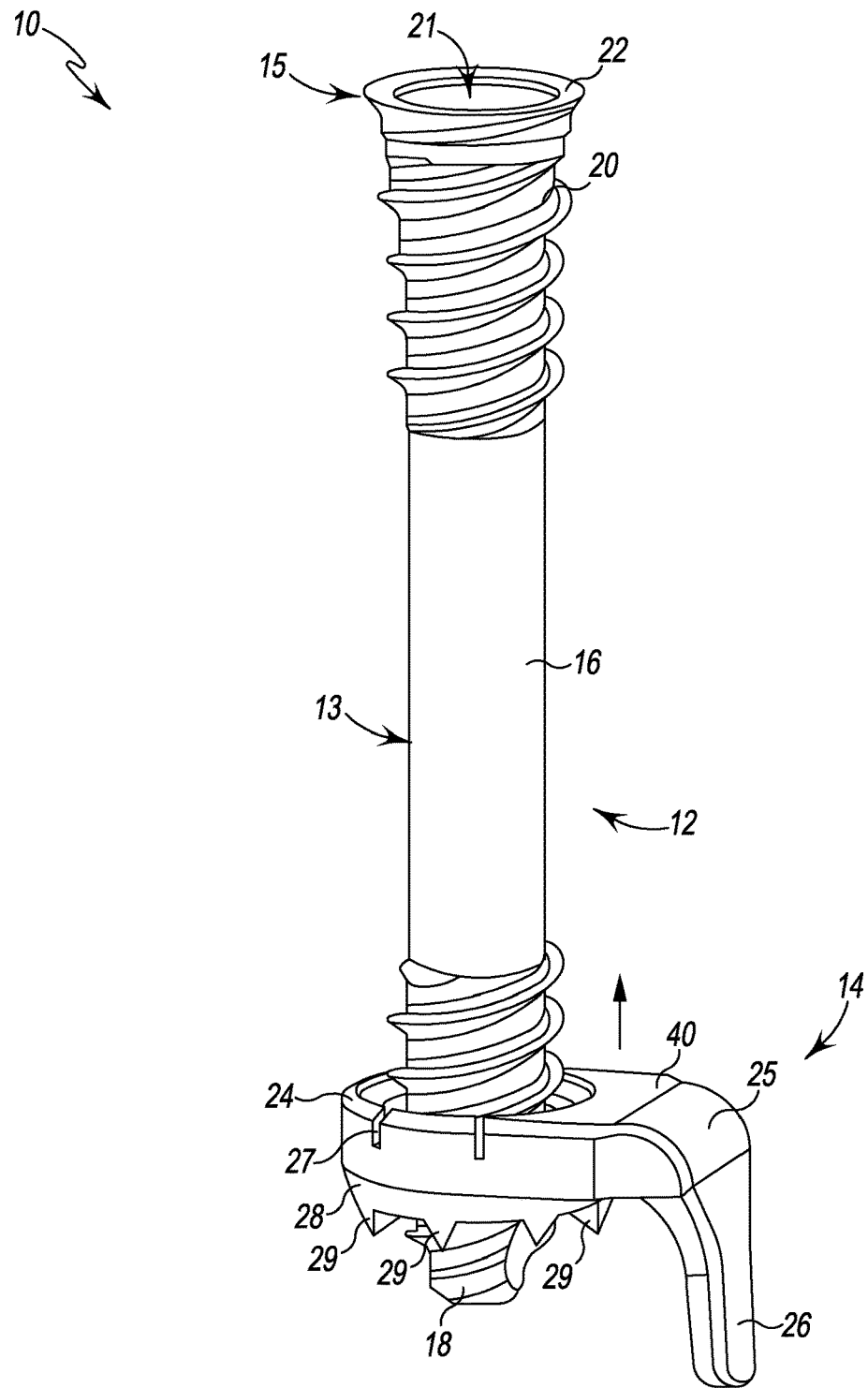
FIG. 5 is an isometric view of the compression screw system of FIG. 1 wherein the hook component is being received by the compression screw component.

The hook component 14 is characterized by a body 23 having an annular head 24 that forms an opening sized to allow the shank 13 of the compression screw component 12 to pass through the opening (see FIG. 5). However, and as explained in greater detail below, the annular head 24 and its opening is sized and configured to capture the head portion 15 of the compression screw component 12. The body 23 has a neck 40 that extends from a radial side of the annular head 24 with a transition portion 25 extending from the neck 40. An elongated flange 26 having a generally tapered and blunt end extends downwardly from the transition portion 25 generally transverse to the neck 40, thereby providing a hook or hook structure with the neck 40 and elongate flange 26 defining a hook area. The length of the neck 40 and the configuration of the flange 26 defines the size of the hook area. The hook may be positioned as desired along an extremity bone or bone portion to provide compression against the extremity bone or bone portion and thus stabilization.

The hook component 14 also has an anti-rotation feature that provides rotational stability of the hook component 14 once the hook component 14 is driven into the bone. Particularly, a ring 28 is formed on the underside of the annular head 24 having a plurality of spikes 29 that extend downwardly from the ring 28. While the spikes 29 are shown as triangular in shape, spikes of other shapes are contemplated. Moreover, the number and spacing of the spikes 29 may vary.

Moreover, the annular head 24 of the hook component 14 has a plurality of vertical slits, cuts, or slots 27 positioned around its upper end. The vertical slits 27 help create structure of the annular head 24/hook component 14 which cooperates with the head portion structure of the compression screw structure described above to provide a 'snap' fit of the annular head 24/hook component 14 onto the compression screw head portion 15 of the compression screw component 12. The vertical slits 27 provide flexibility to the annular head 24 by allowing it to slightly deform (e.g. expand) when radial pressure is exerted against its inside surface 41, and because of the resilient nature of the material for the annular head 24, allow the annular head 24 to return to its original shape when the radial pressure ceases, thereby providing the 'snap' fit of the hook component 14 to the compression screw component 12. The radial pressure is provided by a rib 34 on the inside surface 41 of the annular head 24. The annular head structure thus also includes the radially inwardly projecting rib 34, with the rib 34 preferably, but not necessarily, forming a continuous ring around the inside surface 41 of the annular head 24. The length or depth of the rib 34 from the inside wall 41 of the annular head 24 is such as to allow the rib 34 'snap fit' into the groove 37 of the compression screw as described herein. An upper surface 35 of the rib 34 abuts the lower surface 36 of the radially outwardly flared bottom 33 of the head portion 15 of the compression screw component 14 when installed. Moreover, the inside surface 41 is preferably, but not necessarily, radially inwardly angled or tapered as shown. All these and other features are ascertainable by reference to the figures.

It should be appreciated from the above, that the hook component 14 attaches over and onto a desired bone area or portion. The compression screw component 12 extends through the hook component 14 and into the bones or bone portions, providing the ability to stabilize and compress fractures at various positions. Various sizes of the hook component 14 can be placed on various sizes of the compression screw component 12 depending on the specific anatomy.

Referring now to FIGS. 8-16, there is shown another an implant, generally designated 50, for compressing and/or stabilizing a bone or bones of the extremities and, particularly, a compression screw system 50 for stabilizing and/or compressing bone fractures (or the like) of the extremities at various positions. The compression screw system comprises a compression screw component 52 and a hook component 54. The compression screw component 52 and the hook component 54 are fashioned from a known biocompatible implant material.

The compression screw component 52 comprises a bone screw characterized by an elongated body, shaft or shank 53 with a middle portion 56 having a smooth outer surface, a tip 57 having external threads or threading 58, and a head 75. The threads or threading 58 of the tip 57 is configured to be preferably self-tapping and of a pitch and radial size that provides good gripping of the bone into which the compression screw component 52 is received. A socket 71 is provided in the top 62 of the head 75 of the compression screw component 52. The socket 71 is configured to receive a working end of a compression screw driver or tool (not shown) such as is known in the art. In the figures, the socket 71 is shown as a hexagonal socket. Other configures, however, may be used.

Figure 10:
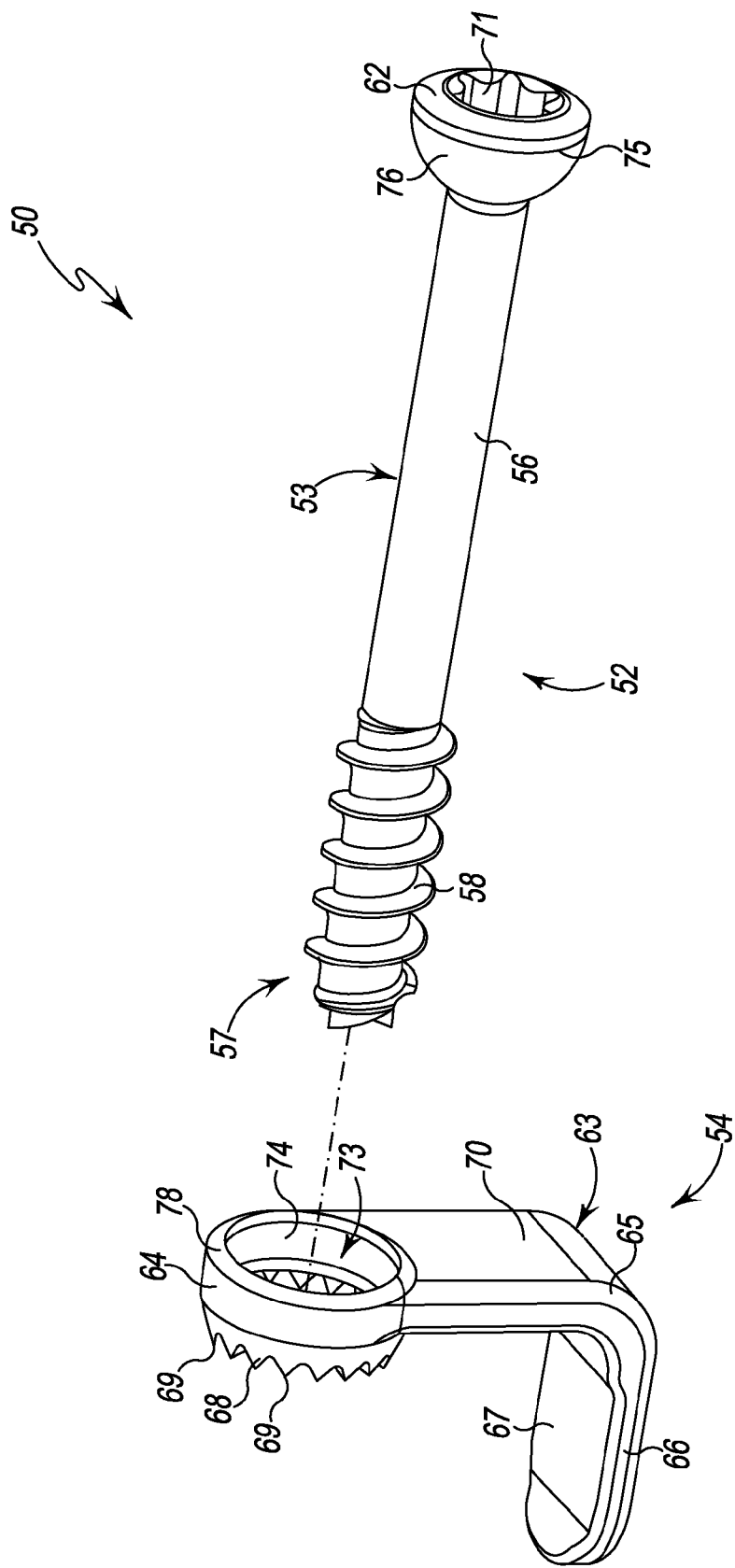
FIG. 10 is an exploded isometric view of the compression screw system of FIG. 8.
Figure 11:
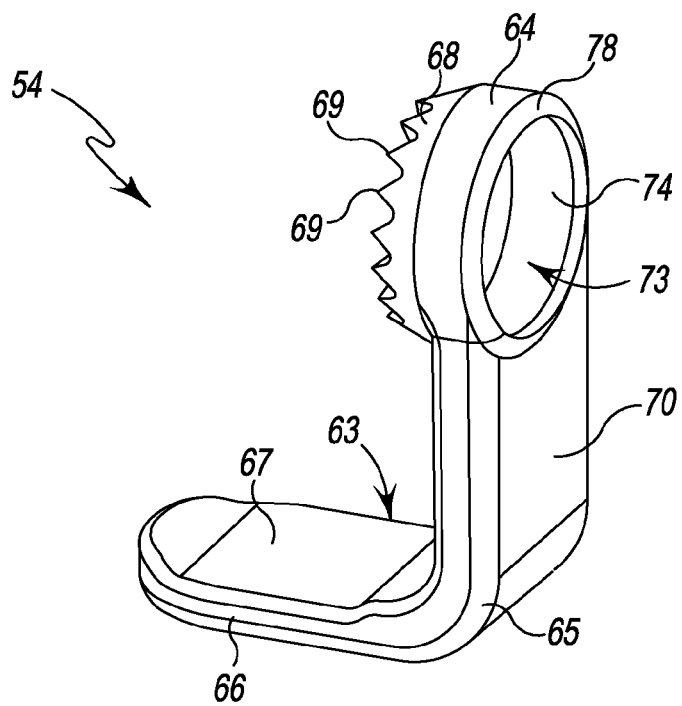
FIG. 11 is an enlarged isometric view of the hook component of the compression screw system of FIG. 8.
Figure 12:
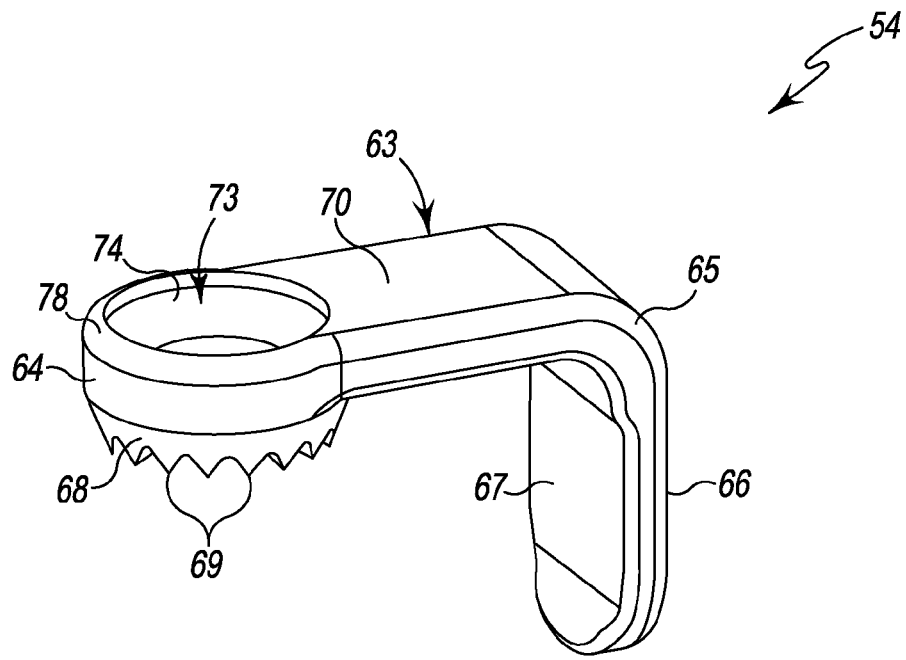
FIG. 12 is another enlarged isometric view of the hook component of the compression screw system of FIG. 8.
Figure 13:
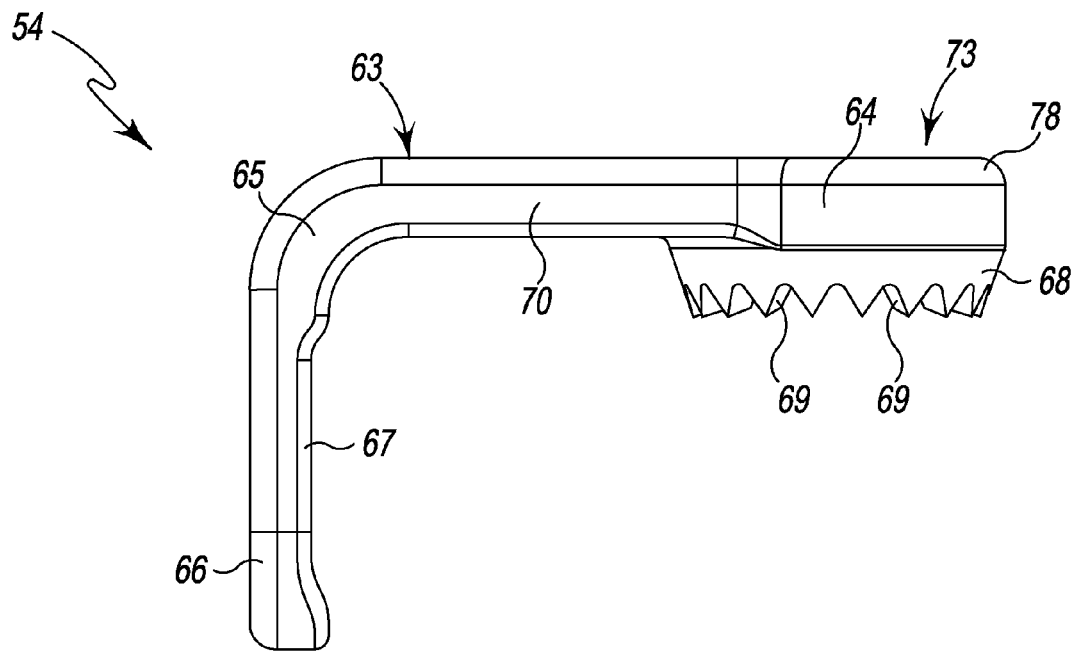
FIG. 13 is an enlarged side view of the hook component of the compression screw system of FIG. 8.
Figure 14:
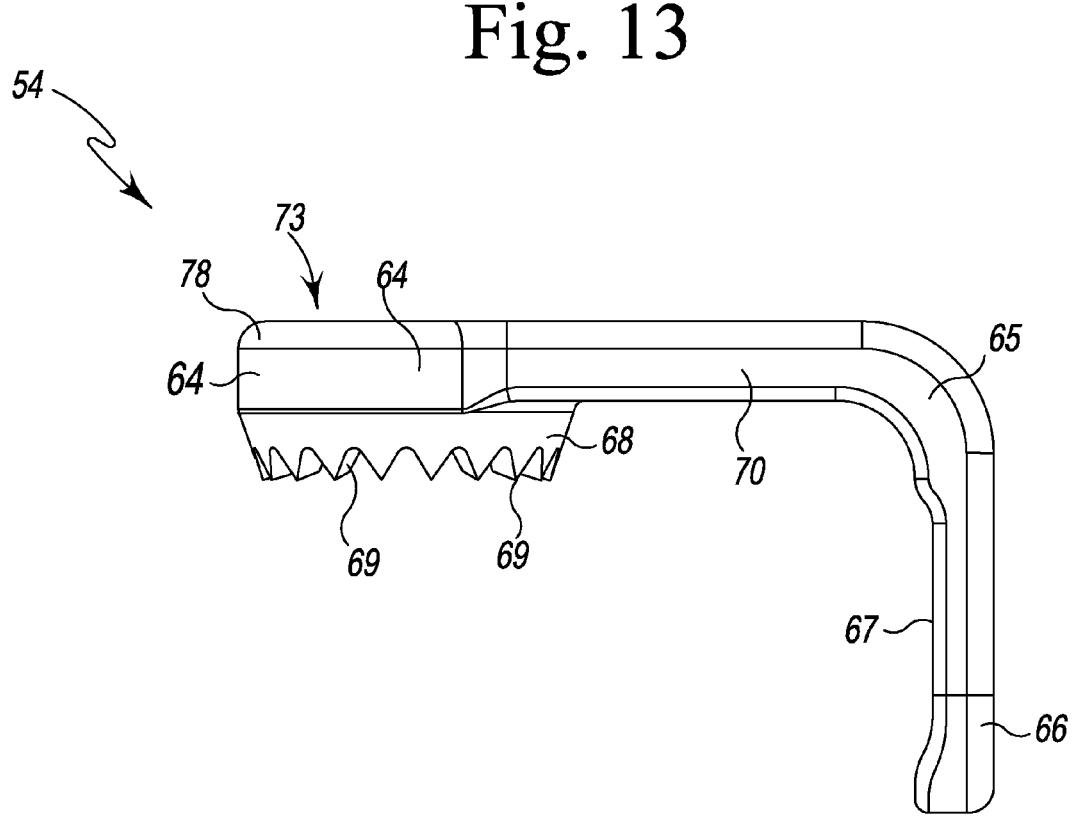
FIG. 14 is another enlarged side view of the hook component of the compression screw system of FIG. 8.
Figure 15:
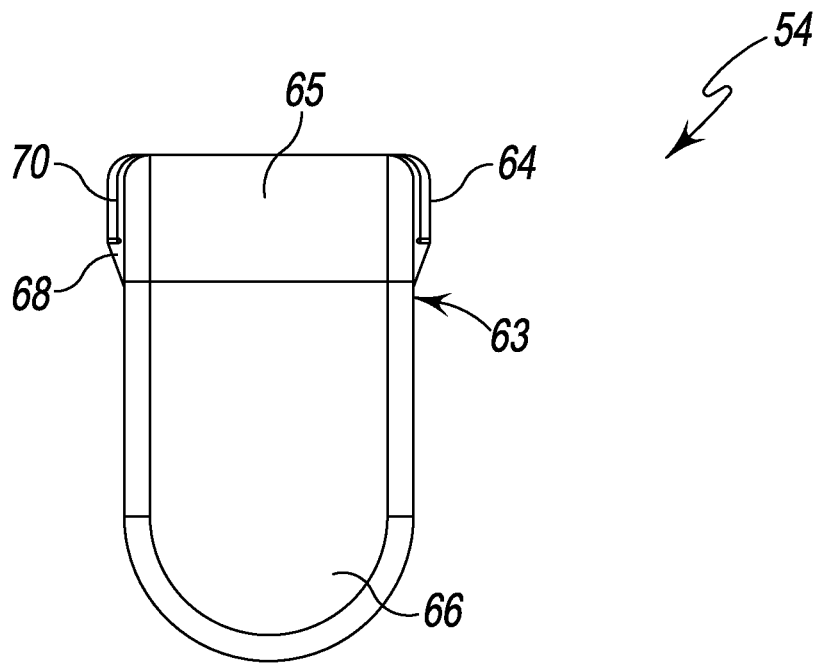
FIG. 15 is an enlarged front view of the hook component of the compression screw system of FIG. 8.
Figure 16:
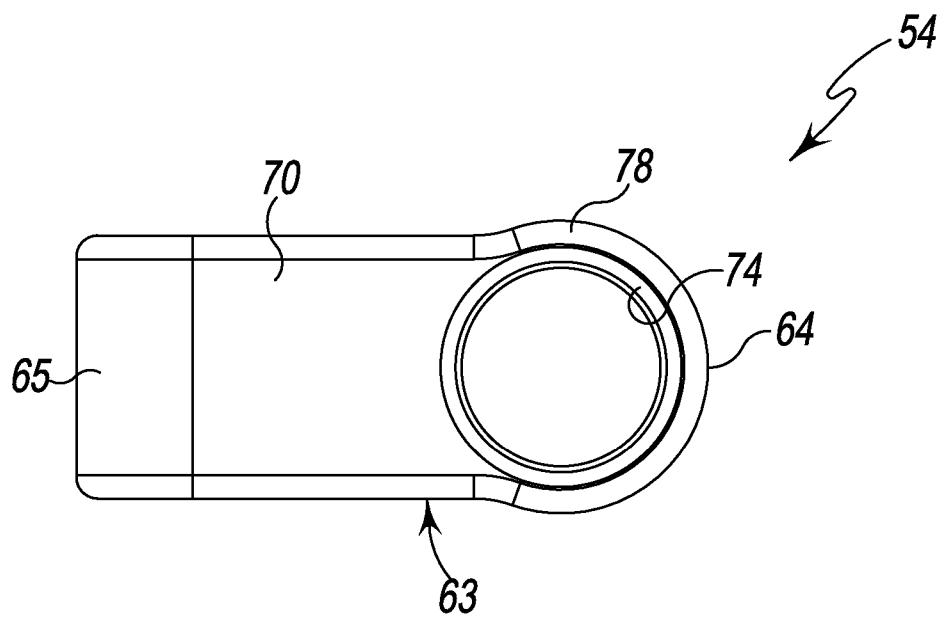
FIG. 16 is an enlarged top view of the hook component of the compression screw system of FIG. 8.
Figure 17:
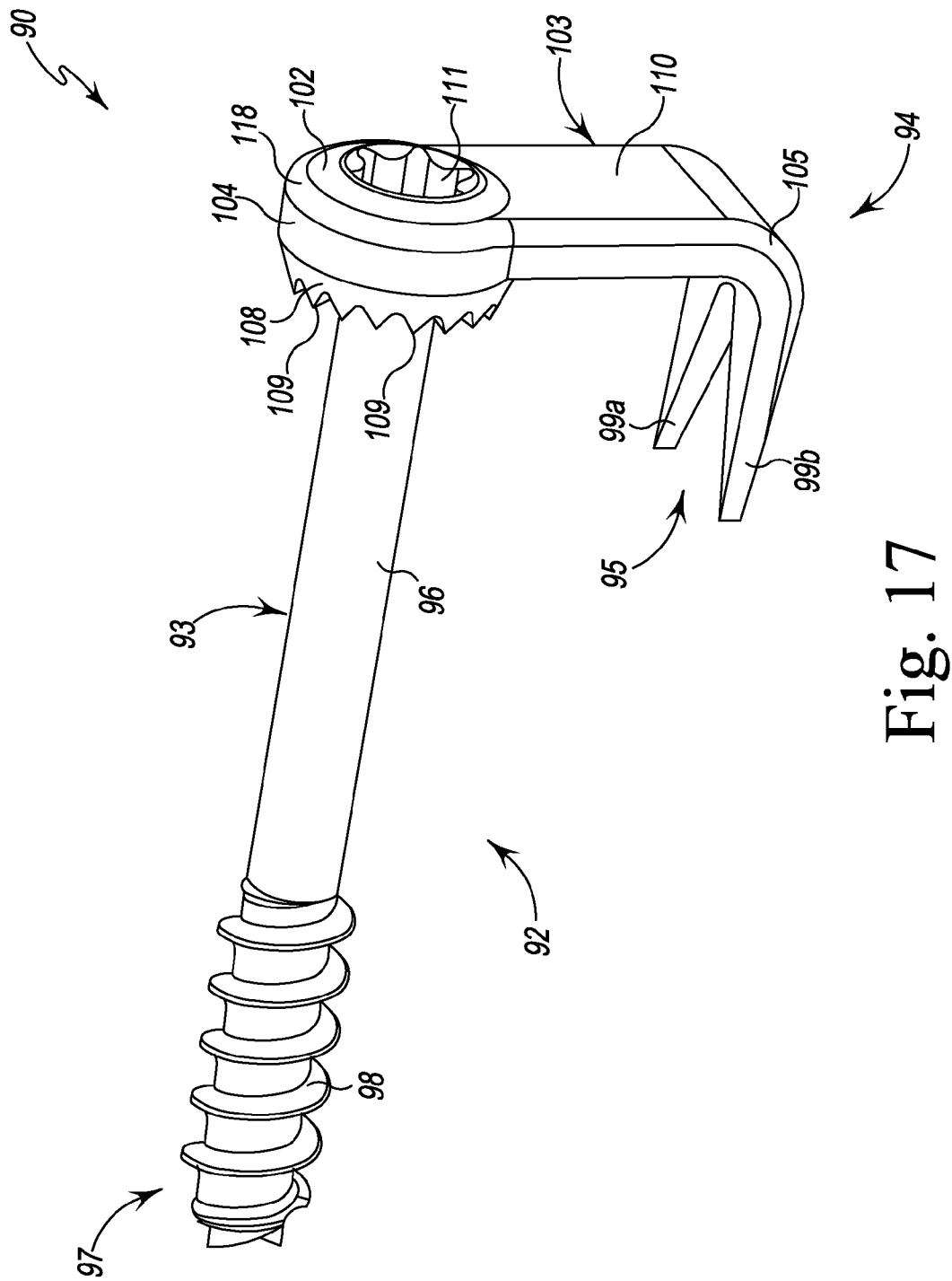
FIG. 17 is an isometric view of a compression screw system for bones of the extremities fashioned in accordance with the principles of the present invention.
Figure 18:
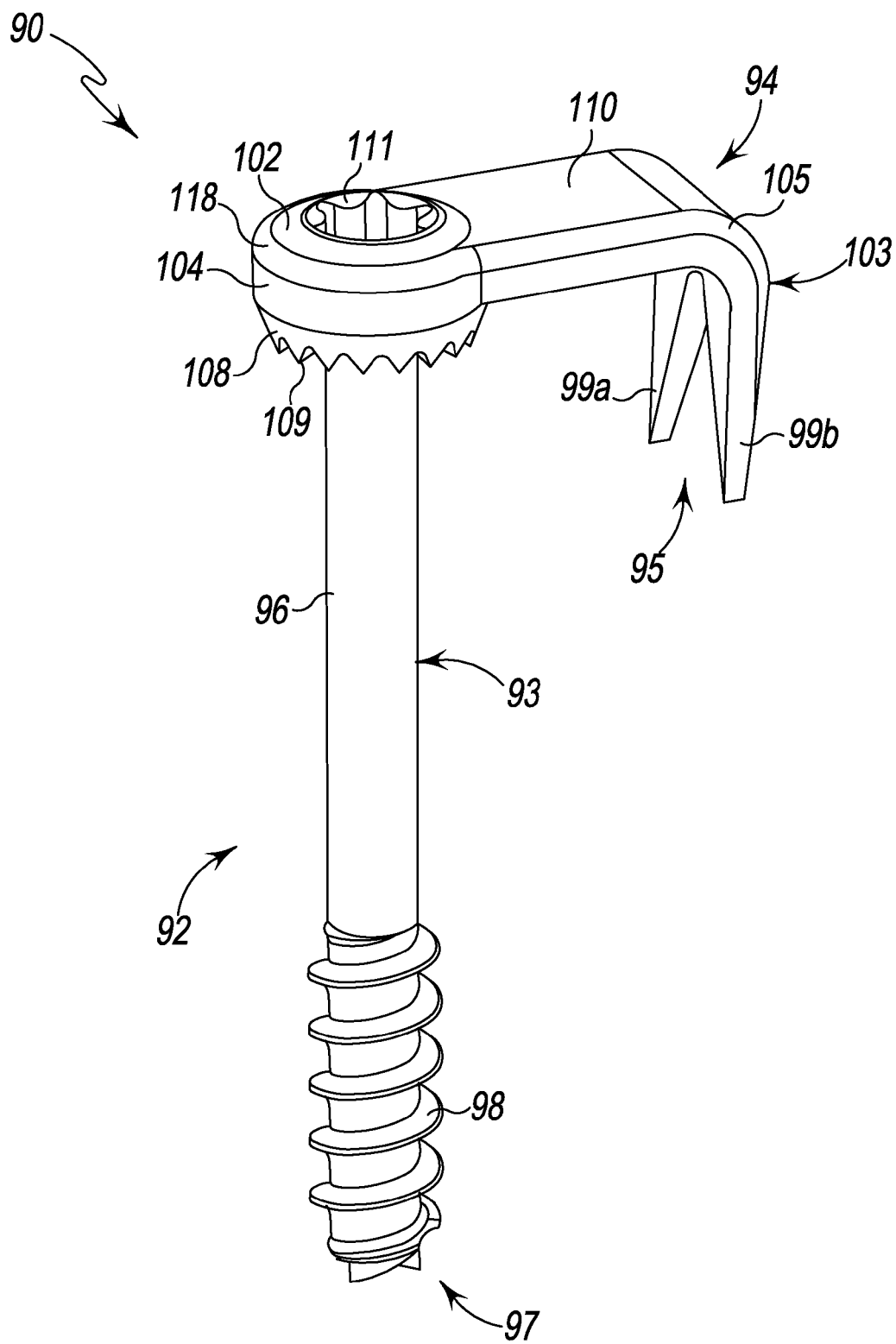
FIG. 18 is another isometric view of the compression screw system of FIG. 17.

As best seen in FIG. 10, the head 75 of the compression screw component 52, includes structure which cooperates with structure of the hook component 54 (described in greater detail below) whereby the hook component 54 is engaged by the compression screw component 52 when the hook component 54 is loaded onto the compression screw component 52 from the bottom of the compression screw component 52 or vice versa. The cooperating structure of the head 75 comprises a rounded or curved underside 76 that extends from the top 62 of the head 75 to the top of the shank 53. In this form, unlike the compression screw system 10, the top of the shank 53 does not include threads or threading. The rounded underside 76 is configured to be received by the hook component 54 and to allow the compression screw component 52 to push against, engage, or provide compression to the hook component 54. In this manner, driving the compression screw component 52 into the extremity bones also secures the hook component 54 at and to the desired portion of an extremity bone.

The hook component 54 is characterized by a body 63 having an annular head 64 that forms an opening 73 sized to allow the shank 53 of the compression screw component 52 to pass through the opening 73 (see FIG. 10). The annular head 64 and its opening 73 is sized and configured to capture the head 75 of the compression screw component 52. The body 63 has a neck 70 that extends from a radial side of the annular head 64 with a transition portion 65 extending from the neck 70. An elongated flange 66 having a generally blunt end extends downwardly from the transition portion 65 generally transverse to the neck 70, thereby providing a hook or hook structure with the neck 70 and elongate flange 66 defining a hook area. The flange 66 may have a concavity 67 on its inside surface. The length of the neck 70 and the configuration of the flange 66 defines the size of the hook area. The size of the end of the flange 66 provides various amounts of bone contact. The size of the flange 66 of the compression screw system 50 is larger than the size of the flange 26 of the compression screw system 10. The hook may be positioned as desired along an extremity bone or bone portion to provide compression against the extremity bone or bone portion and thus stabilization.

The head 64 of the body 63 of the hook component 54 preferably, but not necessarily, has a beveled upper end or top 78. The opening 73 has a beveled surface 74 that is complementary to the curved underside 76 of the head 75 of the compression screw component 52 to allow the head 75 to engage the hook component 54 in a ball and socket relationship. The beveled surface 74 is this sized to capture the head 75 of the compression screw 53.

The hook component 54 also has an anti-rotation feature that provides rotational stability of the hook component 54 once the hook component 54 is driven into the bone. Particularly, a ring 68 is formed on the underside of the annular head 64 having a plurality of spikes 69 that extend downwardly from the ring 68. While the spikes 69 are shown as triangular in shape, spikes of other shapes are contemplated. Moreover, the number and spacing of the spikes 69 may vary.

Referring now to FIGS. 17-23 there is shown another an implant, generally designated 90, for compressing and/or stabilizing a bone or bones of the extremities and, particularly, a compression screw system 90 for stabilizing and/or compressing bone fractures (or the like) of the extremities at various positions. The compression screw system comprises a compression screw component 92 and a hook component 94. The compression screw component 92 and the hook component 94 are fashioned from a known biocompatible implant material.

The compression screw component 92 comprises a bone screw characterized by an elongated body, shaft or shank 93 with a middle portion 96 having a smooth outer surface, a tip 97 having external threads or threading 98, and a head 115. The threads or threading 98 of the tip 97 is configured to be preferably self-tapping and of a pitch and radial size that provides good gripping of the bone into which the compression screw component 92 is received. A socket 111 is provided in the top 102 of the head 115 of the compression screw component 92. The socket 111 is configured to receive a working end of a compression screw driver or tool (not shown) such as is known in the art. In the figures, the socket 111 is shown as a hexagonal socket. Other configures, however, may be used.

Figure 19:
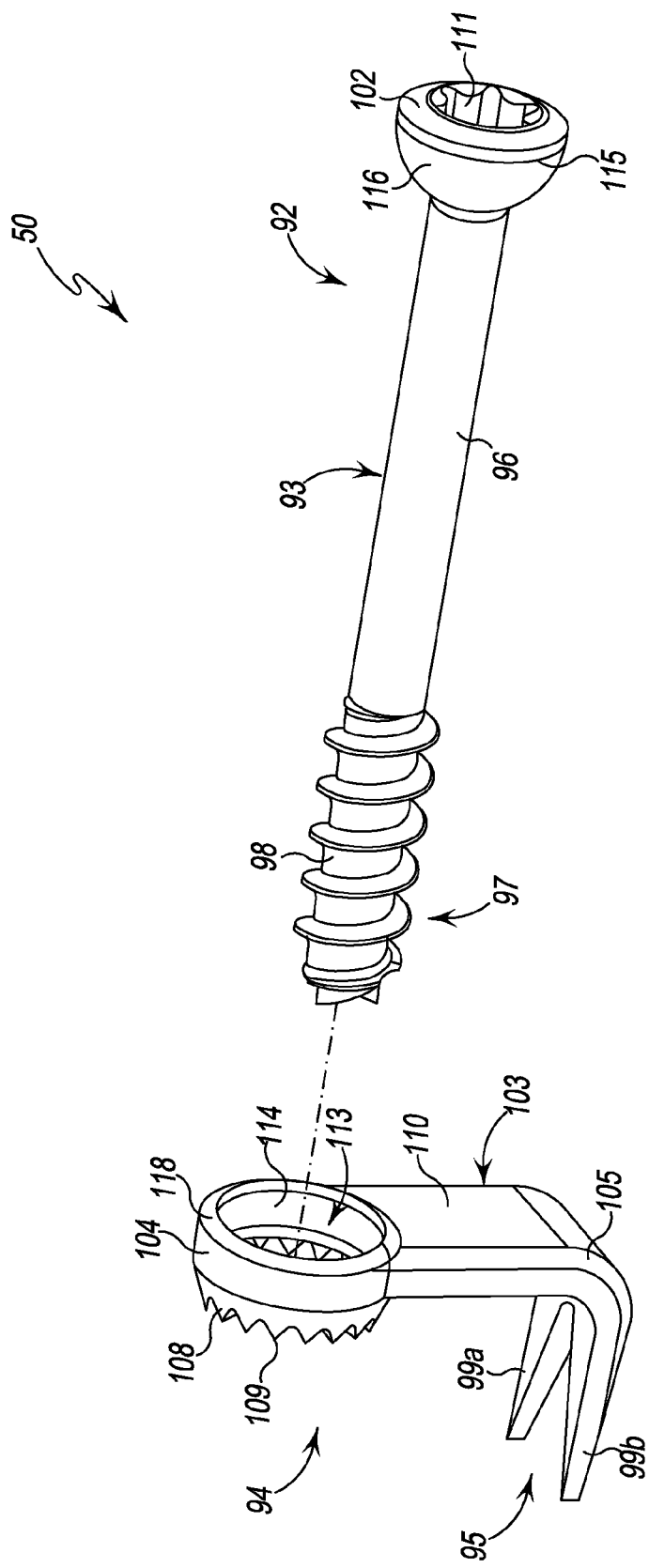
FIG. 19 is an exploded isometric view of the compression screw system of FIG. 17.
Figure 20:
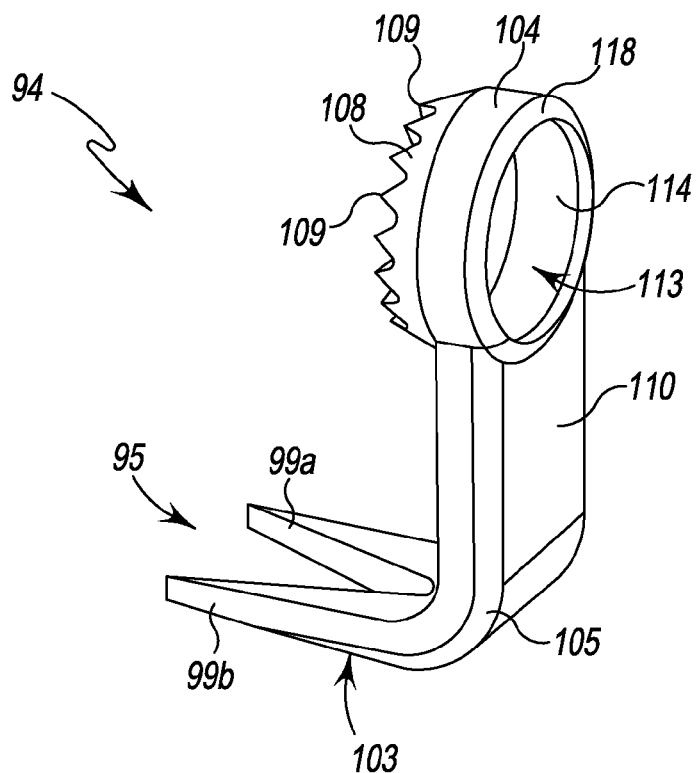
FIG. 20 is an enlarged isometric view of the hook component of the compression screw system of FIG. 17.

As best seen in FIG. 19, the head 115 of the compression screw component 92, includes structure which cooperates with structure of the hook component 94 (described in greater detail below) whereby the hook component 94 is engaged by the compression screw component 92 when the hook component 94 is loaded onto the compression screw component 92 from the bottom of the compression screw component 92 or vice versa. The cooperating structure of the head 115 comprises a rounded or curved underside 116 that extends from the top 102 of the head 115 to the top of the shank 93. In this form, unlike the compression screw system 90, the top of the shank 93 does not include threads or threading. The rounded underside 116 is configured to be received by the hook component 94 and to allow the compression screw component 92 to push against, engage, or provide compression to the hook component 94. In this manner, driving the compression screw component 92 into the extremity bones also secures the hook component 94 at and to the desired portion of an extremity bone.

The hook component 94 is characterized by a body 103 having an annular head 104 that forms an opening 113 sized to allow the shank 93 of the compression screw component 92 to pass through the opening 113 (see FIG. 19). The annular head 104 and its opening 113 is sized and configured to capture the head 115 of the compression screw component 92. The body 93 has a neck 110 that extends from a radial side of the annular head 94 with a transition portion 105 extending from the neck 110. An elongated flange/flange structure 95 having a bifurcated end of two pointed tines 99*a*, 99*b* that extend downwardly from the transition portion 105 generally transverse to the neck 110, thereby providing a hook or hook structure with the neck 110 and elongate flange 95 defining a hook area. The length of the neck 110 and the configuration of the flange 95 defines the size of the hook area. The size of the end of the flange 95 provides various amounts of bone contact. The hook may be positioned as desired along an extremity bone or bone portion to provide compression against the extremity bone or bone portion and thus stabilization.

The head 104 of the body 103 of the hook component 94 preferably, but not necessarily, has a beveled upper end or top 118. The opening 113 has a beveled surface 114 that is complementary to the curved underside 116 of the head 115 of the compression screw component 92 to allow the head 115 to engage the hook component 94 in a ball and socket relationship. The beveled surface 114 is this sized to capture the head 115 of the compression screw 93.

The hook component 94 also has an anti-rotation feature that provides rotational stability of the hook component 94 once the hook component 94 is driven into the bone. Particularly, a ring 108 is formed on the underside of the annular head 104 having a plurality of spikes 109 that extend downwardly from the ring 108. While the spikes 109 are shown as triangular in shape, spikes of other shapes are contemplated. Moreover, the number and spacing of the spikes 109 may vary.

Figure 21:
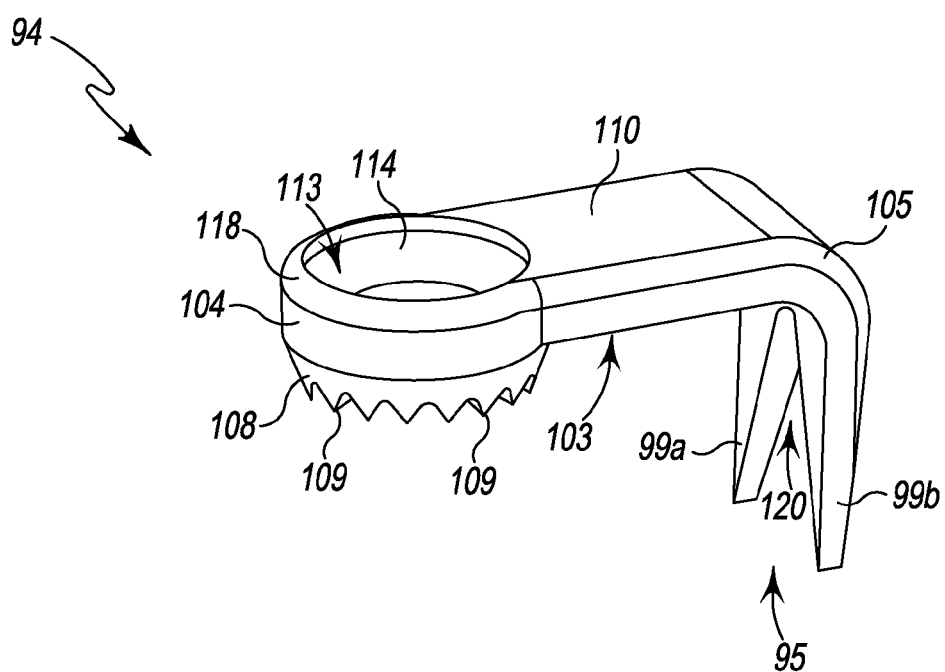
FIG. 21 is another enlarged isometric view of the hook component of the compression screw system of FIG. 17.
Figure 22:
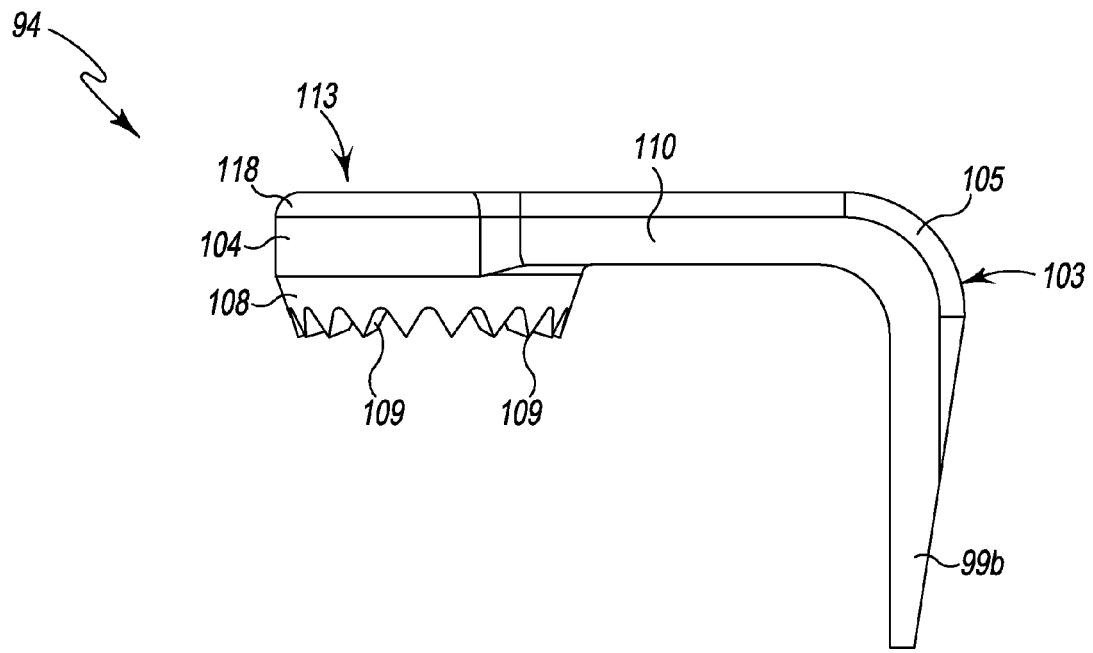
FIG. 22 is an enlarged side view of the hook component of the compression screw system of FIG. 17.
Figure 23:
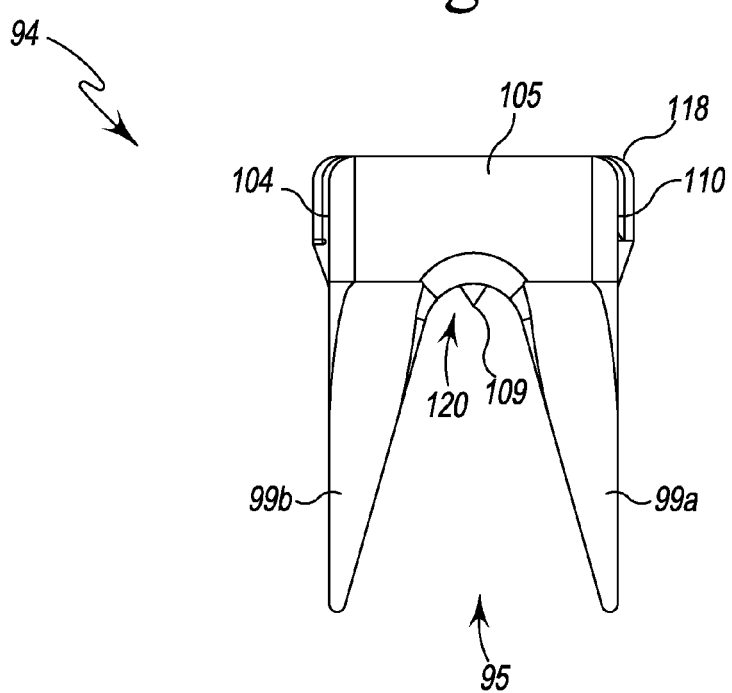
FIG. 23 is an enlarged rear view of the hook component of the compression screw system of FIG. 17.

As best seen in FIGS. 21 and 23, the two tines 99*a*, 99*b* define a cavity 120 therebetween.

Figure 24:
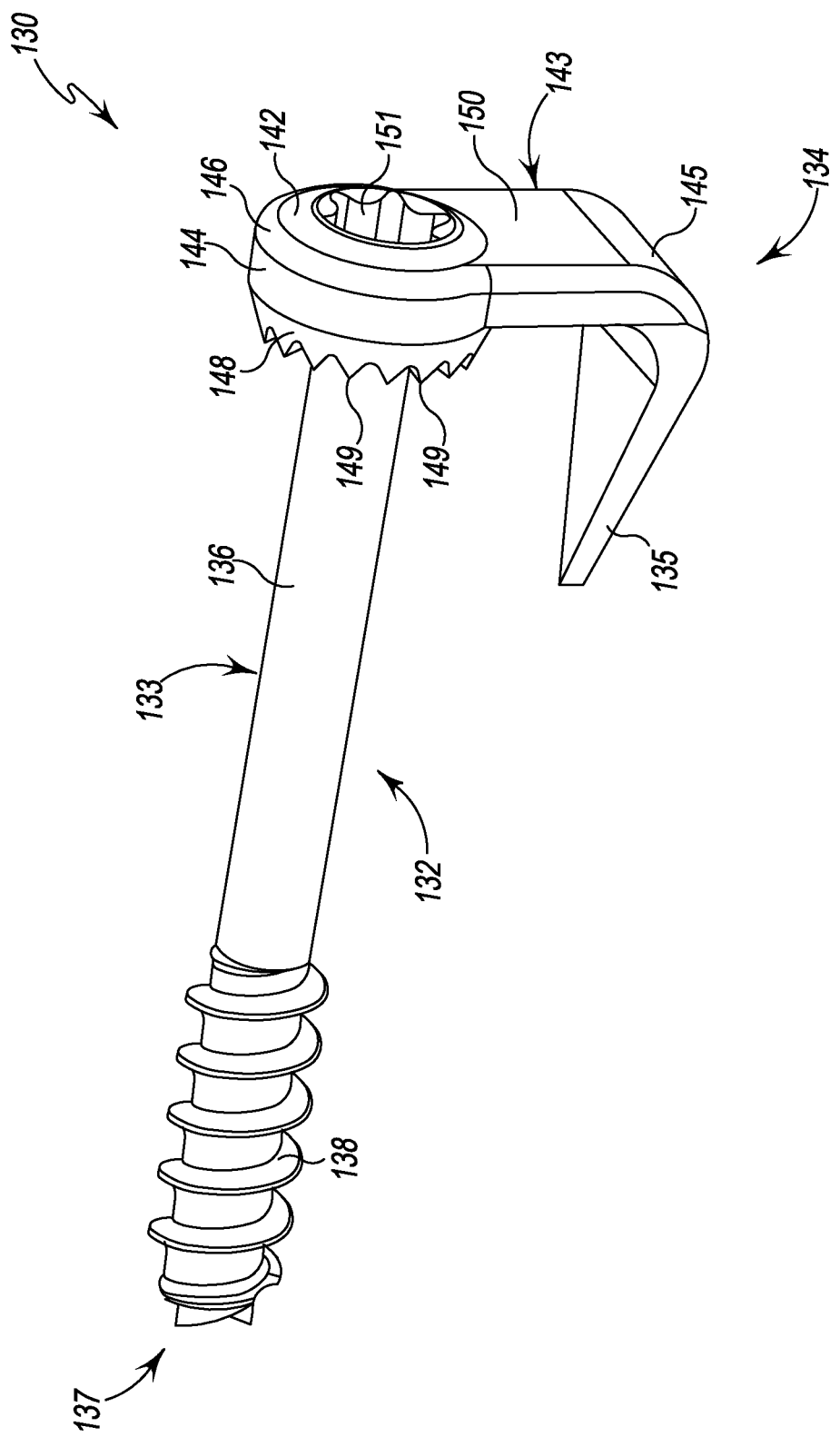
FIG. 24 is an isometric view of a compression screw system for bones of the extremities fashioned in accordance with the principles of the present invention.
Figure 25:
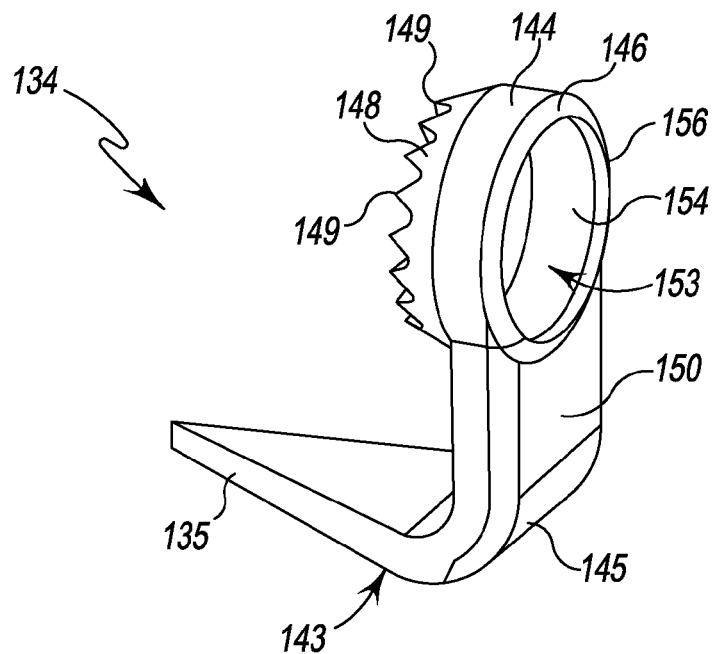
FIG. 25 is an enlarged isometric view of the hook component of the compression screw system of FIG. 24.
Figure 26:
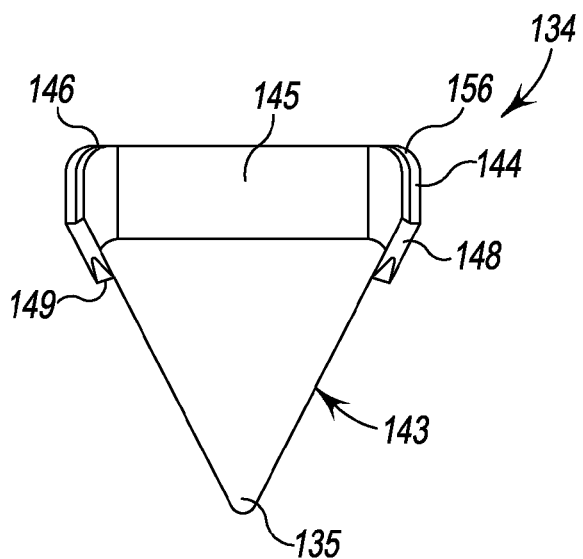
FIG. 26 is an enlarged front view of the hook component of the compression screw system of FIG. 24.

Referring now to FIGS. 24-26, there is shown another an implant, generally designated 130, for compressing and/or stabilizing a bone or bones of the extremities and, particularly, a compression screw system 130 for stabilizing and/or compressing bone fractures (or the like) of the extremities at various positions. The compression screw system comprises a compression screw component 132 and a hook component 134. The compression screw component 132 and the hook component 134 are fashioned from a known biocompatible implant material.

The compression screw component 132 comprises a bone screw characterized by an elongated body, shaft or shank 133 with a middle portion 136 having a smooth outer surface, a tip 137 having external threads or threading 138, and a head 142. The threads or threading 138 of the tip 137 is configured to be preferably self-tapping and of a pitch and radial size that provides good gripping of the bone into which the compression screw component 132 is received. A socket 151 is provided in the top of the head 142 of the compression screw component 132. The socket 151 is configured to receive a working end of a compression screw driver or tool (not shown) such as is known in the art in order to install the compression screw component 132 and the hook component 134 (i.e. to implant the compression screw system 130). In the figures, the socket 151 is shown as a hexagonal socket. Other configures, however, may be used.

While not shown, in like manner to the head 115 of the compression screw component 92 (see e.g. FIG. 19), the head 142 of the compression screw component 132 includes structure which cooperates with structure of the hook component 134 whereby the hook component 134 is engaged by the compression screw component 132 when the hook component 134 is loaded onto the compression screw component 132 from the bottom of the compression screw component 132 or vice versa. The cooperating structure of the head 142 comprises a rounded or curved underside (not seen in the figures) that extends from the top of the head 142 to the top of the shank 133. In this form, unlike the compression screw system 10 (see e.g. FIG. 1), the top of the shank 133 does not include threads or threading. The rounded underside of the head 142 is configured to be received by the hook component 134 and to allow the compression screw component 132 to push against, engage, or provide compression to the hook component 134. In this manner, driving the compression screw component 132 into the extremity bones also secures the hook component 134 at and to the desired portion of an extremity bone.

The hook component 134 is characterized by a body 143 having the generally annular head 144 that has an opening 153 sized to allow the shank 133 of the compression screw component 132 to pass through the opening 153. The head 144 and its opening 153 are sized and configured to capture the head 142 of the compression screw component 132. The body 143 has a neck 150 that extends from a radial side of the annular head 144 with a transition portion 145 extending from the neck 150. An elongated flange 135 having a pointed end extends downwardly from the transition portion 145 generally transverse to the neck 150, thereby providing a hook or hook structure with the neck 150 and elongate flange 135 defining a hook area. The flange 135 is generally smooth on its inside surface, but may be textured or otherwise configured to enhance contact between the flange 135 and bone. The length of the neck 150 and the configuration of the flange 135 defines the size of the hook area. The hook may be positioned as desired along an extremity bone or bone portion to provide compression against the extremity bone or bone portion and thus stabilization.

The head 144 of the body 153 of the hook component 134 preferably, but not necessarily, has a beveled upper end or top 146. The opening 153 has a beveled surface 154 that is complementary to the curved underside of the head 142 of the compression screw component 132 to allow the head 142 to engage the hook component 134 in a ball and socket relationship. The beveled surface 154 is this sized to capture the head 142 of the compression screw 133.

The hook component 134 also has an anti-rotation feature that provides rotational stability of the hook component 134 once the hook component 134 is driven into the bone. Particularly, a ring 148 is formed on the underside of the annular head 144 having a plurality of spikes 149 that extend downwardly from the ring 148. While the spikes 149 are shown as triangular in shape, spikes of other shapes are contemplated. Moreover, the number and spacing of the spikes 149 may vary.

It should be appreciated from the above, that the hook component 134 attaches over and onto a desired bone, bones, bone area or portion(s). The compression screw component 132 extends through the hook component 134 and into the bone, bones, bone area or portion(s), providing the ability to stabilize and compress fractures at various positions. Various sizes of the hook component 134 can be placed on various sizes of the compression screw component 132 depending on the specific anatomy.

Figure 27:
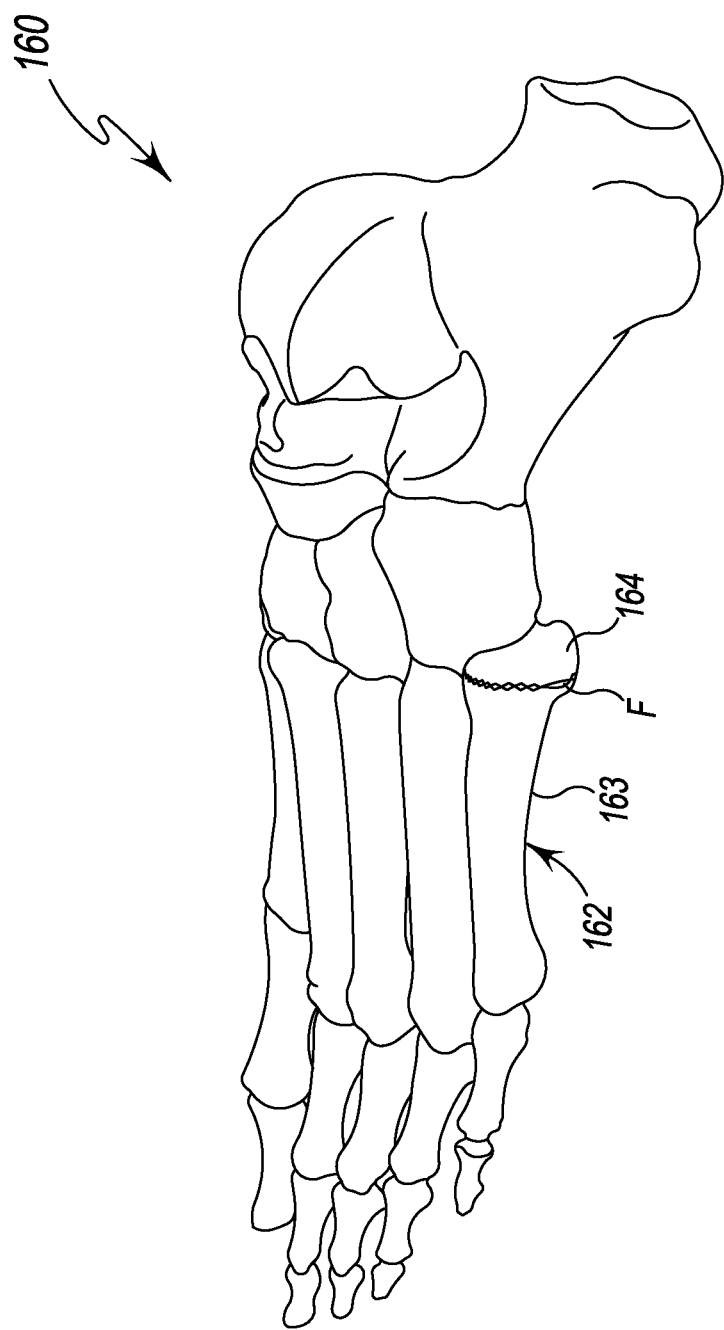
FIG. 27 is a side view of bones of a left foot with the fifth metatarsal thereof having a fracture.
Figure 28:
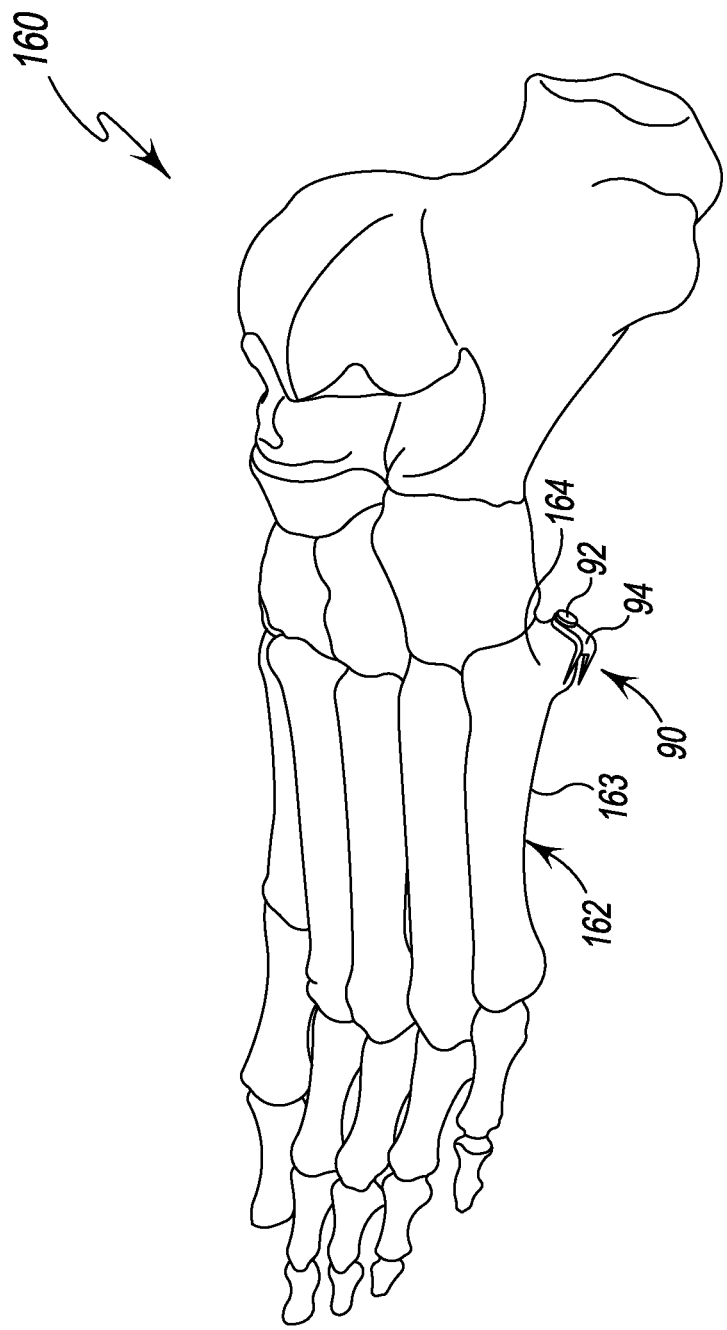
FIG. 28 is the side view of the bones of the left foot of FIG. 27 with a compression screw system fashioned in accordance with the present principles implanted to mend the fifth metatarsal fracture.
Figure 29:
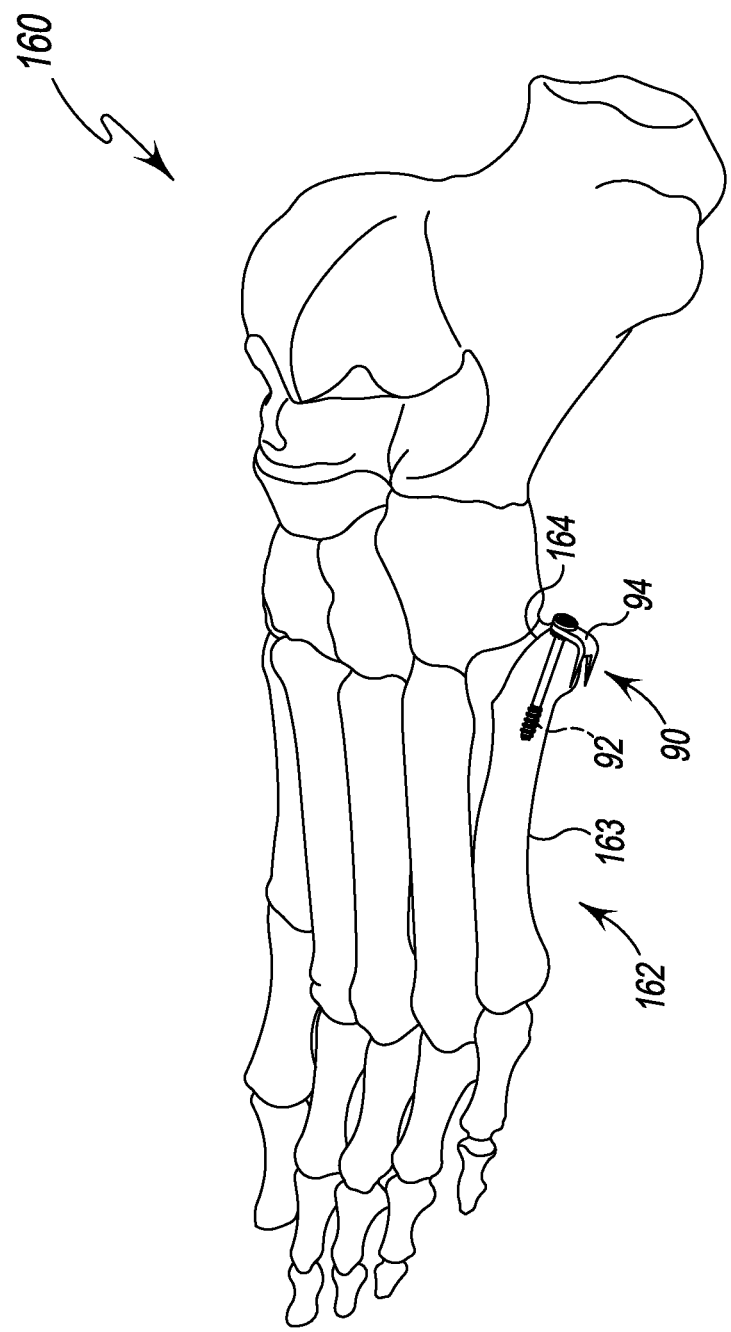
FIG. 29 is the side view of the bones of the left foot of FIG. 28 with the implanted compression screw system with the fifth metatarsal in shadow.

FIG. 27 shows the bones of a left human foot 160 wherein the fifth metatarsal 162 has a fracture or break F thus dividing the fifth metatarsal 162 into two bone portions 163 and 164. FIG. 28 shows the bones of the left foot 160 of FIG. 27 wherein the bone compression screw system 90 has been implanted through the bone portions 164 and 163 in order to compress and stabilize the two bone portions 164, 163. FIG. 29 shows the bones of the left foot with the implanted compression screw system 90 of FIG. 28 with the fifth metatarsal 162 shown in ghost in order to see the entire compression screw system 90 as implanted.

It should be appreciated that although the present bone implant system has been described in particularity with respect to foot bones, it is applicable to hand bones and those bones being very similar in anatomy. It should also be appreciated that dimensions of the compression screw systems and their components and/or features can be altered as desired.

What is claimed is:

1. A compression screw system for bones of the extremities, the compression screw system comprising:
   a compression screw component; and
   a hook component;
   the compression screw component having a shaft, a tip on a distal end of the shaft, bone screw threading about the tip, and a screw head on a proximate end of the shaft, the head having a top with a configured socket, and a curved undersurface extending from a bottom of the screw head to the shaft; and
   the hook component comprising:
      an annular head defining a bore with an angled inlet configured complementary to the curved undersurface of the compression screw head, a plurality of spikes extending axially from and positioned radially about an outlet of the bore, and
      a body extending from a radial side of the annular head, the body comprising:
         a neck extending transverse to the radial side of the annular head, and
         an elongated flange (a) extending from and substantially perpendicular to an end of the neck distal the annular head, and extending (b) substantially parallel to the compression screw component when received in the bore of the annular head;
   wherein the compression screw component is received in the bore of the annular head of the hook component and engaging the hook component to compress against bone when installed;
   wherein the elongated flange includes an inner side facing the compression screw component, and an outer side opposite the inner side, the inner side of the elongated flange having a concave surface facing the compression screw component.

2. The compression screw system of claim 1, wherein the elongated flange has a blunt end.

3. The compression screw system of claim 1, wherein the concave surface extends along a substantial portion of the elongated flange.

4. The compression screw system of claim 3, wherein the neck and elongated flange define a hook area.

5. The compression screw system of claim 1, wherein the annular head comprises a beveled upper end.

6. The compression screw system of claim 5, wherein the beveled upper end extends beyond a first surface of the neck.

7. The compression screw system of claim 6, wherein the annular head comprises a ring having the plurality of spikes extending therefrom, the ring extending beyond a second surface of the neck.

8. The compression screw system of claim 1, wherein the elongated flange extends substantially parallel to the compression screw component when the compression screw component is received in the hook component.

9. The compression screw system of claim 3, wherein the annular head comprises a beveled upper end.

10. The compression screw system of claim 9, wherein the beveled upper end extends beyond a first surface of the neck.

11. The compression screw system of claim 9, wherein the annular head comprises a ring having the plurality of spikes extending therefrom, the ring extending beyond a second surface of the neck.

12. The compression screw system of claim 3, wherein the elongated flange extends substantially parallel to the compression screw when the compression screw is received in the hook.

13. A compression screw system for providing stabilization and compression of bones of the extremities, the compression screw system comprising:
   a compression screw having a shaft, a tip on a distal end of the shaft, bone screw threading about the tip, and a screw head on a proximate end of the shaft, the head having a top with a configured socket, and a curved undersurface extending from a bottom of the screw head to the shaft; and
   a hook comprising:
      an annular head defining a bore with an angled inlet configured complementary to the curved undersurface of the compression screw head, a plurality of spikes extending axially from and positioned radially about an outlet of the bore, and
a body extending from a radial side of the annular head, the body comprising:
a neck extending transverse to the radial side of the annular head, and
an elongated flange (a) extending from and substantially perpendicular to an end of the neck distal the annular head, and extending (b) substantially parallel to the compression screw component when received in the bore of the annular head;
wherein the compression screw is received in the bore of the annular head and engaging the hook to compress against bone when installed;
wherein the elongated flange includes an inner side facing the compression screw, and an outer side opposite the inner side, the inner side of the elongated flange having a concave surface facing the compression screw component.

14. The compression screw system of claim 13, wherein the elongated flange has a blunt end.

15. The compression screw system of claim 13, wherein the concave surface extends along a substantial portion of the elongated flange.

16. The compression screw system of claim 15, wherein the neck and elongated flange define a hook area.

* * * * *